US007668688B2

(12) United States Patent
Najim Al-Khamis

(10) Patent No.: US 7,668,688 B2
(45) Date of Patent: Feb. 23, 2010

(54) SYSTEM, PROGRAM PRODUCT, AND RELATED METHODS FOR ESTIMATING AND MANAGING CRUDE GRAVITY IN REAL-TIME

(75) Inventor: Mohammed Najim Al-Khamis, Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 31 days.

(21) Appl. No.: 12/140,868

(22) Filed: Jun. 17, 2008

(65) Prior Publication Data

US 2009/0312963 A1 Dec. 17, 2009

(51) Int. Cl.
G01L 7/00 (2006.01)
G01N 9/36 (2006.01)

(52) U.S. Cl. .................. 702/138; 73/61.44; 436/32; 702/136; 702/137

(58) Field of Classification Search ............ 702/45, 702/47, 50, 136–138; 73/1.16, 32, 36, 61.44, 73/438; 356/301; 436/32; 250/461.1; 137/7, 137/10, 15.12, 317, 318
See application file for complete search history.

(56) References Cited

U.S. PATENT DOCUMENTS

| 3,033,040 | A | 5/1962 | Piros |
| 3,453,868 | A | 7/1969 | Williams, Jr. |
| 3,483,732 | A | 12/1969 | Gogarty |
| 4,248,599 | A | 2/1981 | Mommessin |
| 4,417,474 | A | 11/1983 | Elderton |
| 5,182,940 | A | 2/1993 | Bailey |
| 5,394,339 | A | 2/1995 | Jones |
| 6,550,327 | B1 | 4/2003 | Van Berk |
| 6,633,043 | B2 | 10/2003 | Hegazi |
| 6,687,643 | B1 | 2/2004 | Cason |
| 6,734,963 | B2 | 5/2004 | Gamble |
| 6,807,857 | B2 | 10/2004 | Storm |
| 7,032,449 | B2 | 4/2006 | Rivas |
| 2003/0226395 | A1 | 12/2003 | Storm, Jr. et al. |
| 2004/0139791 | A1 | 7/2004 | Johansen |

(Continued)

FOREIGN PATENT DOCUMENTS

CN 1338587 7/2001

(Continued)

OTHER PUBLICATIONS

International Search Report and Written Opinion, Application No. PCT/US2009/047639, dated Nov. 24, 2009.

*Primary Examiner*—John H Le
(74) *Attorney, Agent, or Firm*—Bracewell & Giuliani LLP

(57) ABSTRACT

Systems, program product, and methods to estimate and manage flowing fluid characteristics of a fluid stream flowing through a pipeline in real-time, are provided. A system can include a vertically oriented extent of a pipeline for transporting crude oil, a pair of spaced vertically apart sensors or sensor assemblies connected to a bypass line interfaced with or positioned across the vertically oriented extent of the pipeline to obtain pressure and temperature readings of the crude oil flowing through the pipeline, a controller in communication with the pair of sensors or sensor assemblies, and crude oil analysis and management program product stored in the memory of the controller and adapted to determine or estimate density, specific gravity, and API gravity of the crude oil to thereby manage flowing fluid characteristics of the crude oil.

30 Claims, 8 Drawing Sheets

U.S. PATENT DOCUMENTS

2008/0257413 A1 * 10/2008 Noureldin et al. ............ 137/10

FOREIGN PATENT DOCUMENTS

| | | |
|---|---|---|
| EP | 352203 | 1/1990 |
| GB | 2041542 A | 9/1980 |
| JP | 63132134 | 4/1988 |
| WO | 9504869 | 2/1995 |
| WO | 9961887 A1 | 12/1999 |

* cited by examiner

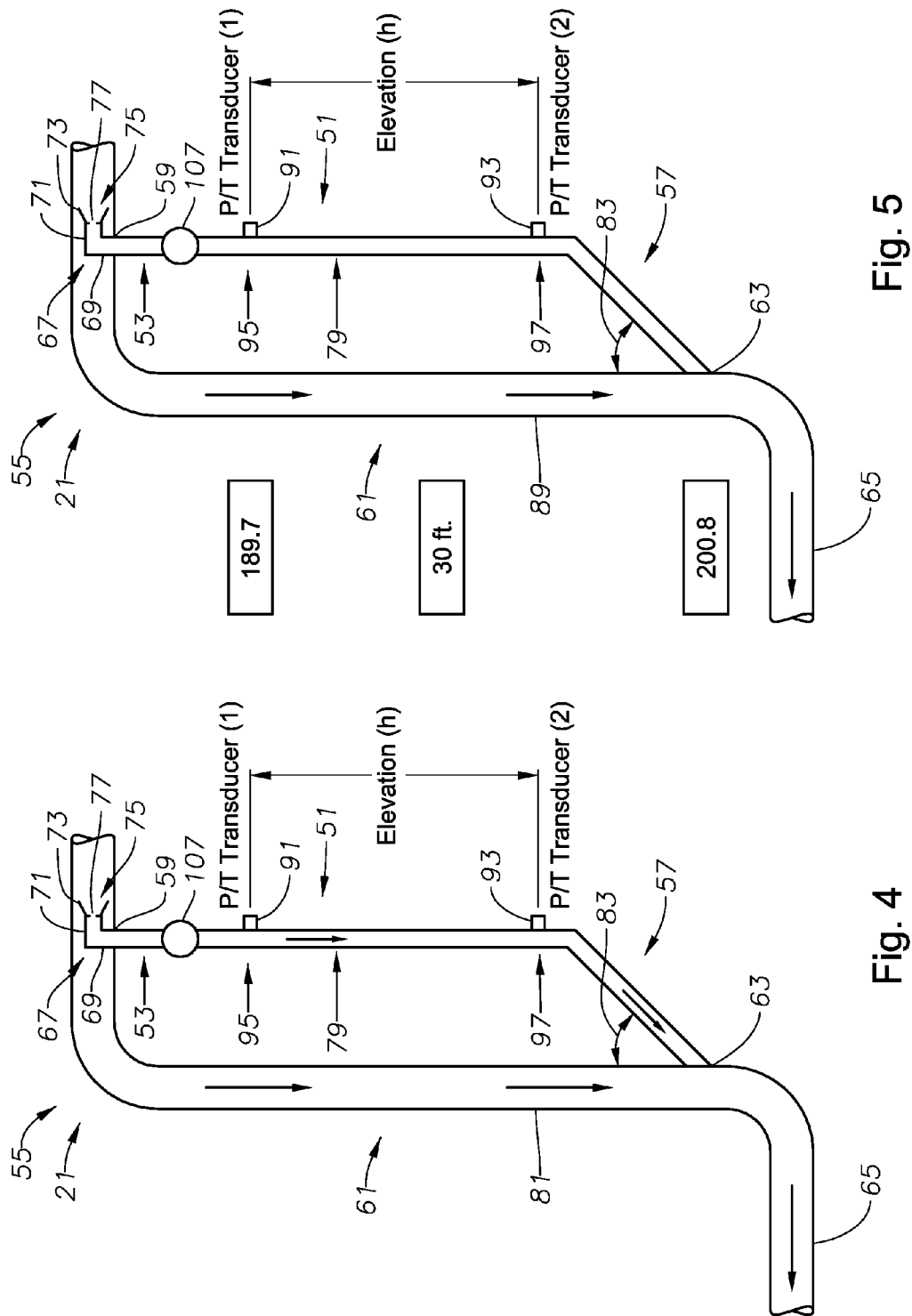

SYSTEM, PROGRAM PRODUCT, AND RELATED METHODS FOR ESTIMATING AND MANAGING CRUDE GRAVITY IN REAL-TIME

BACKGROUND OF THE INVENTION

1. Field of the Invention

The present invention relates generally to managing fluid characteristics of a fluid, and specifically to systems, apparatus, program product, and methods to estimate and manage flowing fluid characteristics of a fluid stream flowing through a pipeline.

2. Description of Related Art

Crude oil generally comprises a complex mixture of hydrocarbons of the various molecular weights plus other organic compounds of variable specific gravity and viscosity. Crude oil, however, also includes various impurities including gas, water, salt, etc. along with other chemical compounds used in the extraction process. Accordingly, crude oil received from production wells is typically routed through a processing facility such as, for example, a gas oil separation plant (GOSP). Such gas oil separation plant can include, for example, a 2 or 3-stage oil-gas separation facility, with a 2 or 3-stage dehydrator/desalting train. A typical gas oil separation plant processes ~300 MBD of crude and ~100 MBD of water. The gas oil separation plants are generally designed to handle watercuts up to 30%, and some have been modified and retrofitted to handle higher watercuts. The crude oil exiting the gas oil separation plant is considered dehydrated dead crude oil.

Crude oil extracted from each separate oil well for processing at the gas oil separation plant, has generally been found to have its own unique characteristics. Responsively, in order to classify the oil coming from each separate oil well, the oil industry has developed various methodologies of grading the different types of crude oil. One of the most popular methodologies is the use of a grading system based on specific gravity/density developed by the American Petroleum Institute (API), a U.S trade association representing various companies involved in production, refinement, and distribution of oil and gas. According to such methodology, each volume of crude oil is assigned an API degree rating or grade which relates its specific gravity with that of water. According to the API scale, water is assigned a 10 degree API rating.

Crude oil is classified as light, medium, or heavy, according to its measured API gravity, with the lighter crude oil assigned a higher API gravity. In general, crude oil having a rating above approximately 31 API is considered in the industry to be "light," with oil having a rating (grade) above approximately 40 API considered to be "very light." Crude oil having an API gravity between approximately 22 and 31 API is considered in the industry to be "medium." Crude oil having an API gravity below approximately 22 is considered in the industry to be "heavy." Various other rating schemes are used to further define each specific volume of crude oil. For example, oil having a low sulphur content is identified as being "sweet," while crude oil having a high sulphur content is identified as being "sour."

The commercial value of a volume of crude oil generally depends upon its API gravity degree and on the needs of the buyer. Nevertheless, in general, crude oil having an API gravity of between 40 and 45 API tends to have the greatest commercial value. Accordingly, crude oil producers running multiple wells may wish to control production of the individual wells so that the overall deliverable volume of crude oil is maintained within a selected range of values or at least maintained above a minimum value.

Conventional practice to determine the API gravity, so far, is to collect fluid samples and to send the samples to a laboratory for manual fluid density estimation. Because, in most of the cases, the crude grade for a certain field does not change much (i.e., production from the same reservoir/reservoirs may have almost similar crude grades), this manual method is generally considered quite practical. The inventor has recognized, however, that for cases with a complex crude blend (i.e., mix of several produced crude grades) from several wells, for example, the manual method is not practical. In this case, a real time estimation of crude grade is required in order to ensure that the required produced crude grade is met at all times, and to facilitate adjusting the flow rates of certain wells with specific crude grades in order to maintain or to bring the overall produced crude grade back to the required or desired limit if outside such limit.

Other newly developed methodologies of determining API gravity, exist. For example, U.S. Pat. No. 6,633,043 by Hegazi et al., titled "Method for Characterization of Petroleum Oils Using Normalized Time-Resolved Fluorescence Spectra," describes a method based on time-resolved, laser-induced fluorescence spectroscopy for the characterization and fingerprinting of petroleum oils and other complex mixtures. The method depends on exciting the wavelength-resolved fluorescence spectra of manually obtained samples using ultraviolet pulsed laser radiation, measuring them at specific time gates within the temporal response of the excitation laser pulse, and comparing them in terms of their shapes, alone, without taking into account their relative intensities. U.S. Pat. No. 4,248,599 by Mommessin et al., titled "Process for Determining the API gravity of Oil by FID" describes determining the API gravity of a manually obtained oil sample by vaporizing its volatile and pyrolyzable components, measuring the ratio of the amount vaporized within a range of relatively high temperatures to the total amount vaporized. Again, the inventor has recognized that for cases with a complex crude blend (i.e., mix of several produced crude grades), such manual methodologies are not practical.

Although not understood by the inventor as being recognized in industry as an acceptable method for obtaining an API gravity of a complex blend of crude oil, the inventor recognizes that various methodologies of determining density of a fluid, nevertheless, exists. For example, U.S. Pat. No. 6,807,857, by Storm Jr. et al., titled "Method and Apparatus for Determining Density of a Flowing Fluid" describes a tool and process for measuring the density of a flowing fluid using two sets of measurement readings each taken from a corresponding pair of pressure assessment zones of a half-loop configured fluid conducting tool. WO 95/04869 by Kyllingstad, titled "A Method and an Apparatus for Measuring Density and Pressure Drop in a Flowing Fluid" similarly describes a pipe loop for receiving fluid from a main flow and having two branches each including a pair of spaced apart pressure sensors which provide data to calculate the liquids density and pressure loss per length unit. CN 13385, by Wang, titled "In-Line Continuous Measuring Method for Concentration and Density of Liquid Medium" describes a method and apparatus for measuring density which includes a vertical measuring tube for receiving an upward vertical flow and having two pressure measuring points, a differential pressure transducer used to measure their differential pressure, a medium temperature transducer positioned in the two pressure measuring points, and an ambient temperature transducer. U.S. Pat. No. 7,032,449 by Rivas, titled "Measurement of Fluid Properties in Vessel and Sensor for Same" describes a sensor for measuring properties of a fluid in a vessel having sensors spaced vertically along the sensor body inserted into a container. U.S. Pat. No. 6,687,643 by Cason Jr., titled "In-situ Sensor System and Method for Data Acquisition in Liquids" describes a system and method which measures the density of a static liquid in a container using pressure sensors positioned at two separate locations and separated by a fixed distance, and a temperature sensor. U.S. Pat. No. 3,033,040 by Piros, titled "Density Measuring Apparatus" describes a density meter for measuring the density of liquids, and controlling the proportion of constituent liquids present in blends so that the blend has a given density. The density meter determines density of fluid mixture extracted by a pump from a main flow using a pressure difference between a pressure maintaining (constant pressure) device positioned at an upper end of a vertical conduit and a pressure measuring device located at its lower end. U.S. Pat. No. 3,483,732 by Gogarty, titled "Continuous Density-Determining Device and Process" describes an apparatus which includes a conduit for extracting fluid to determine its density, a means for rendering a flowing liquid turbulent, a liquid flow measuring device, and a differential pressure transducer to determine a difference in pressure between two pressure points along the conduit.

Each of these devices, however, fails to provide a process for measuring the density of flowing fluid in a main flow line in real-time, and/or requires either an extraction pump, a means to pump fluid upwardly through a vertical component of a sample line, internal pressure sensors, or a combination thereof. Nor does either of these devices provide necessary means for estimating, and thus controlling, API gravity. Recognized by the inventor, therefore, is the need for a process setup that enables real-time estimation of fluid density and crude API gravity of a liquid fluid stream flowing through a pipeline in a processing facility, which does not require the addition of a sampling or extraction pump, or internal pressure sensors.

SUMMARY OF THE INVENTION

In view of the foregoing, embodiments of the present invention advantageously provide a system, apparatus, program product, and methods for estimating and managing flowing fluid characteristics of a fluid stream, in real time, which does not require the addition of a sampling or extraction pump, application of a fluid collector, or use of manual sampling techniques. Embodiments of the present invention also advantageously provide a system, apparatus, program product, and methods to estimate and manage flowing fluid characteristics of a fluid stream of, for example, dehydrated degassed dead crude oil flowing through a pipeline in a processing facility. Embodiments of the present invention advantageously overcome the inadequacies of conventional density measuring equipment through use of a pair of dual pressure-temperature transducers inserted into a pair of vertically spaced apart pressure taps positioned through a vertically oriented (i.e., not substantially horizontal) section of bypass line connected adjacent a vertically oriented portion of a pipeline carrying the crude oil processed by the processing facility.

Embodiments of the present invention provide a system to estimate and manage flowing fluid characteristics of a fluid stream flowing through a pipeline in a processing facility, in real-time. According to an embodiment of the system, the system can include at least a portion of a pipeline for transporting fluid, which can include, for example, dehydrated degassed crude oil received from a plurality of wells and processed by a processing facility. The at least a portion of the pipeline can include a vertically oriented extent substantially vertically oriented so that the crude oil flowing through the vertically oriented extent flows downward through the vertically oriented extent of the pipeline. The system can also include a bypass line having a proximal end portion connected to the pipeline to receive a portion of the fluid stream flowing through the pipeline defining the crude oil sample and having a distal end portion positioned to reintroduce the crude oil sample back into the fluid stream of the pipeline. The system can also include at least one first sensor connected to the at least a portion of the bypass line at a first location along an extent of the bypass line to provide at least one signal indicative of pressure and temperature of the crude oil at the first location, at least one second sensor connected to the at least a portion of the bypass line at a second location along the extent of the bypass line to provide at least one signal indicative of pressure and temperature of the crude oil at the second location. The system can also include a remotely operated valve interfaced with the bypass line and positioned downstream of the proximal end portion connection of the bypass line to the pipeline and upstream of the first location along the extent of the bypass line, and a controller including a processor in communication with the at least one first sensor and the at least one second sensor and adapted to estimate and manage flowing fluid characteristics of the crude oil. The system can further include crude oil analysis and management program product stored in the memory of the controller. The system can still further include a plurality of flow control valves each in communication with the controller either directly or through an engineering station. Each flow control valve is separately positioned to individually control a flow rate of crude oil entering the processing facility, and thus, is positioned to collectively control a flow rate of crude oil entering the at least a portion of the pipeline. As such, according to an embodiment of the system, the crude oil can provide a complex crude blend including a plurality of crude grades provided by the plurality of oil wells.

According to an embodiment of the system, the crude oil analysis and management program product can include instructions that when executed by the processor of the controller, cause the controller to perform the operations of determining fluid pressure and temperature of the crude oil at the first location responsive to the at least one signal provided by the at least one first sensor, determining fluid pressure and temperature of the crude oil at the second location responsive to the at least one signal provided by the at least one second sensor, and estimating density of the crude oil flowing through the at least a portion of the pipeline responsive to: the determined fluid pressure at the first location, the determined fluid pressure at the second location, and the vertical elevation between a pressure sensor portion of the at least one first sensor and a pressure sensing portion of the at least one second sensor. The operations can also include estimating specific gravity of the crude oil flowing through the at least a portion of the pipeline at standard condition responsive to: the estimated density of the crude oil, determined fluid temperature at the first location, and the determined fluid temperature at the second location; and estimating API gravity of the crude oil flowing through the at least a portion of the pipeline at standard condition responsive to the estimated specific gravity of the crude oil flowing through the pipeline. The operations can further include comparing the estimated API gravity of the crude oil flowing through the at least a portion of the pipeline to at least one threshold value to determine if the API gravity has failed to meet the at least one threshold value to thereby maintain the API gravity above a preselected desired minimum value or within a preselected desired range limit, and adjusting the flow rate of one or more of the plurality of wells responsive to determining that the API gravity fails to meet the at least one threshold value.

Embodiments of the present invention also include crude oil analysis and management program product stored in a tangible computer medium to estimate and manage flowing fluid characteristics of a fluid stream flowing through a pipeline in real-time. According to an embodiment of the program product, the program product can include instructions that when executed by a computer, cause the computer to perform the operations of determining fluid pressure of crude oil at a first location along a vertically oriented extent of a bypass line positioned adjacent a vertically oriented extent of the pipeline and carrying a sample of crude oil extracted from a fluid stream flowing through the pipeline responsive to at least one signal provided by at least one first sensor associated with the first location, and determining fluid pressure of the crude oil at a second location responsive to at least one signal provided by at least one second sensor associated with the second location. The operations can also include estimating API gravity of the crude oil flowing through the vertically oriented extent of the pipeline responsive to: the determined fluid pressure at the first location, the determined fluid pressure at the second location, and vertical elevation between the at least one first sensor and the at least one second sensor. The operation of estimating API gravity can include the operations of estimating density of the crude oil flowing through the pipeline, determining fluid temperature of the crude oil at the first location along the vertically oriented extent of the bypass line responsive to the at least one signal provided by the at least one first sensor, determining fluid temperature of the crude oil at the second location along the vertically oriented extent of the responsive to the at least one signal provided by the at least one second sensor, and estimating specific gravity of the crude oil flowing through the pipeline at standard condition responsive to: the estimated density of the crude oil, determined fluid temperature at the first location, and the determined fluid temperature at the second location, to thereby estimate the API gravity of the crude oil at standard at standard conditions.

The operations can further include comparing the estimated API gravity of the crude oil flowing through the pipeline to at least one threshold value to determine if the API gravity has failed to meet the at least one threshold value to thereby maintain the API gravity above a preselected desired minimum value or within a preselected desired range limit; and providing an adjustment signal to adjust a flow rate of one or more of a plurality of wells each having at least one flow control valve each separately positioned to control a flow rate of crude oil entering the pipeline (e.g., via a processing facility) received from a corresponding separate one of the plurality of oil wells.

Embodiments of the present invention also include methods for estimating and managing flowing fluid characteristics of a fluid stream flowing through a pipeline (e.g., in a processing facility), in real-time. According to an embodiment of a method, the method can include the steps of determining fluid pressure and temperature of a flowing fluid (e.g., dehydrated degassed crude oil) at a first location along a vertically oriented extent of a bypass line carrying the dehydrated degassed crude oil flowing downward between a first location and a second location substantially vertically spaced apart from the first location along the vertically oriented extent and vertically below the first location, and determining fluid pressure and temperature of the dehydrated degassed crude oil at the second location along the vertically oriented extent of the bypass line. The fluid pressure at the first location can be determined using a first pressure transducer coupled to a first fluid pressure tap. Similarly, the fluid pressure at the second location can be determined using a second pressure transducer coupled to a second fluid pressure tap and positioned at a predetermined (preselected) vertical elevation below that of the first pressure transducer.

The steps can also include estimating specific gravity of the crude oil sample, and thus, the specific gravity of the crude oil flowing through the pipeline responsive to: the determined fluid pressure at the first location, the determined fluid pressure at the second location, and the vertical elevation between the first location and the second location; and estimating API gravity of the crude oil flowing through the pipeline at standard condition responsive to: the estimated specific gravity of the crude oil flowing through the vertically oriented extent of the pipeline, the determined fluid temperature at the first location, and the determined fluid temperature at the second location. The steps can further include determining or otherwise estimating a density of the crude oil flowing through the vertically oriented extent of the pipeline.

The steps can also include comparing the estimated API gravity of the crude oil flowing through the pipeline to at least one threshold value to determine if the API gravity has failed to meet the at least one threshold value, and adjusting a flow rate of one or more of a plurality of wells supplying the pipeline either directly or through a processing facility responsive to determining that the API gravity fails to meet the at least one threshold value to thereby maintain the API gravity above a preselected desired minimum value or within a preselected desired range limit.

According to another embodiment of a method for estimating and managing flowing fluid characteristics of a fluid stream flowing through a pipeline in real-time, the method can include the steps of determining fluid pressure of crude oil at a first location along a vertically oriented extent of a bypass line connected adjacent to or across a vertical extent of a pipeline carrying the crude oil flowing, and determining fluid pressure at a second location along the vertically oriented extent of the pipeline and vertically below the first location. The fluid pressure can be determined using a first pressure sensor extending through a first portion of an outer wall surface of the pipeline, the fluid pressure at the second location can be determined using a second pressure sensor extending through a second portion of the outer wall surface of the pipeline, and the first and second portions of the outer wall surface of the pipeline can have a predetermined vertical elevation therebetween.

The method can also include the steps of estimating density of the crude oil flowing through the vertically oriented extent of the pipeline responsive to: the determined fluid pressure at the first location, the determined fluid pressure at the second location, and the vertical elevation between the first location and the second location.

The method can also include determining fluid temperature at the first location along the vertically oriented extent of the bypass line, determining fluid temperature at the second location along the vertically oriented extent of the bypass line, estimating specific gravity of the crude oil sample of the flowing through the pipeline at standard condition responsive to the estimated density, determined fluid temperature at the first location, and the determined fluid temperature at the second location; and estimating API gravity of the crude oil flowing through the pipeline at standard condition responsive to the estimated specific gravity of the crude oil flowing through the vertically oriented extent of the pipeline.

The method can still further include comparing the estimated API gravity of the crude oil flowing through the pipeline to at least one threshold value to determine if the API gravity has failed to meet (or has exceeded) the at least one threshold value, and adjusting a flow rate of one or more of the plurality of wells responsive to determining that the API gravity fails to meet (or exceeds) the at least one threshold value to thereby maintain the API gravity above a preselected desired minimum value or within a preselected desired range limit.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 4 is a schematic diagram of a portion of a pipeline and associated bypass line including a pressure and temperature sensor assembly and isolation of (open) according to an embodiment of the present invention;

FIG. 5 is a schematic diagram of the portion of a pipeline and associated bypass line shown in FIG. 4 including a pressure and temperature sensor assembly and isolation of (closed) including exemplary values according to an embodiment of the present invention;

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout.

FIGS. 1-11 illustrate a system, apparatus, program product, and methods for estimating and managing flowing fluid characteristics of a fluid stream flowing through a pipeline in a processing facility in real-time. As will be described or detailed below, various embodiments of the present invention can provide a system, apparatus, program product, and methods which do not require the addition of a sampling or extraction pump or application of a fluid collector. Various embodiments of the present invention also provide a system, apparatus, program product, and methods to estimate and manage flowing fluid characteristics of a fluid stream of fluid in the form of dehydrated degassed dead crude oil flowing through a pipeline in a processing facility. Various embodiments of the present invention beneficially overcome the inadequacies of conventional density measuring equipment through use of a pair of dual pressure-temperature transducers inserted into a pair of vertically spaced apart pressure taps positioned through a vertically oriented (i.e., not substantially horizontal) section of a bypass line positioned to sample crude oil flowing through a main flow pipeline carrying crude oil processed by the processing facility.

Figure 1:
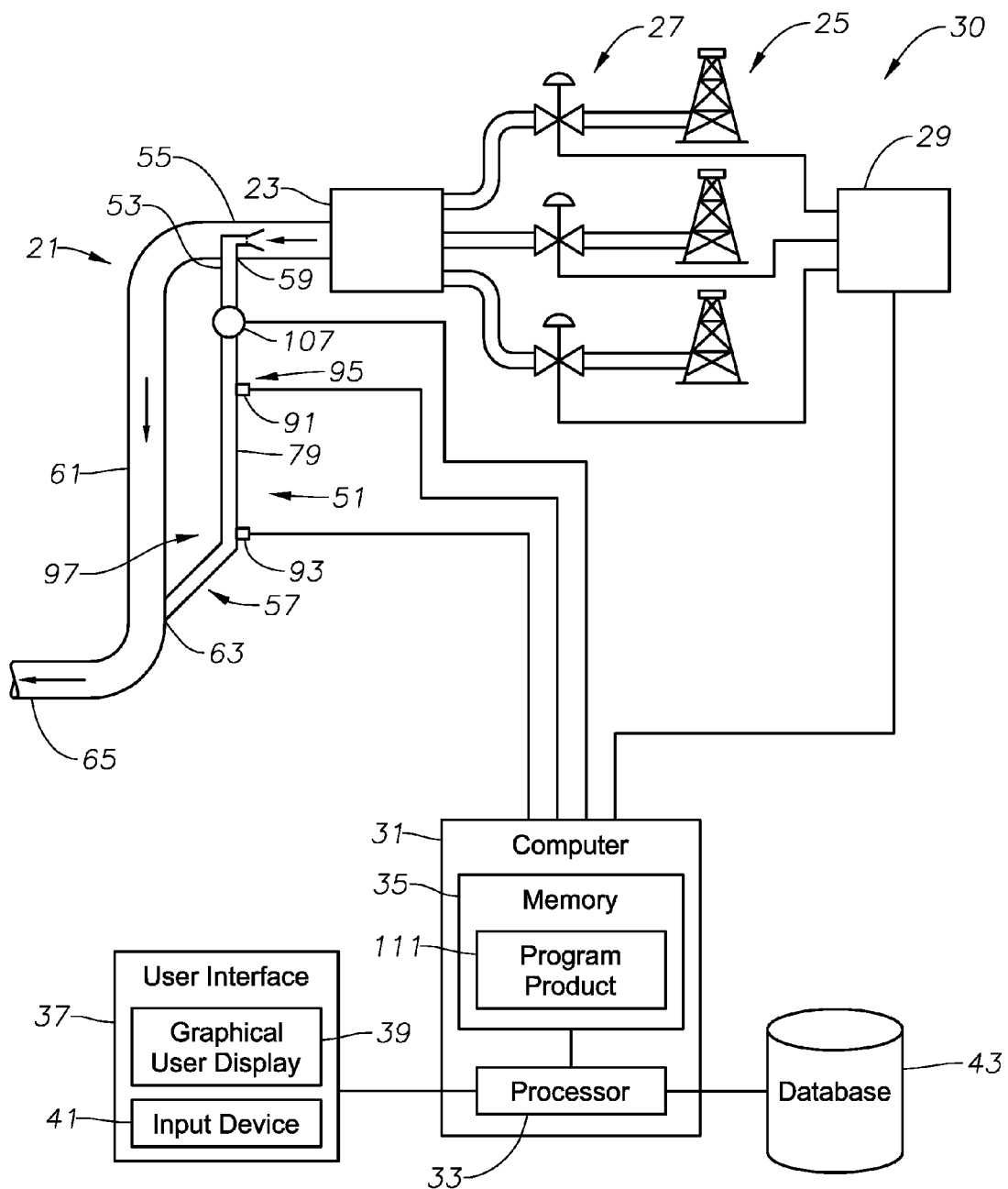
FIG. 1 is a schematic block diagram of a system to estimate and manage flowing fluid characteristics of fluid flowing through a pipeline according to an embodiment of the present invention.
Figure 2:
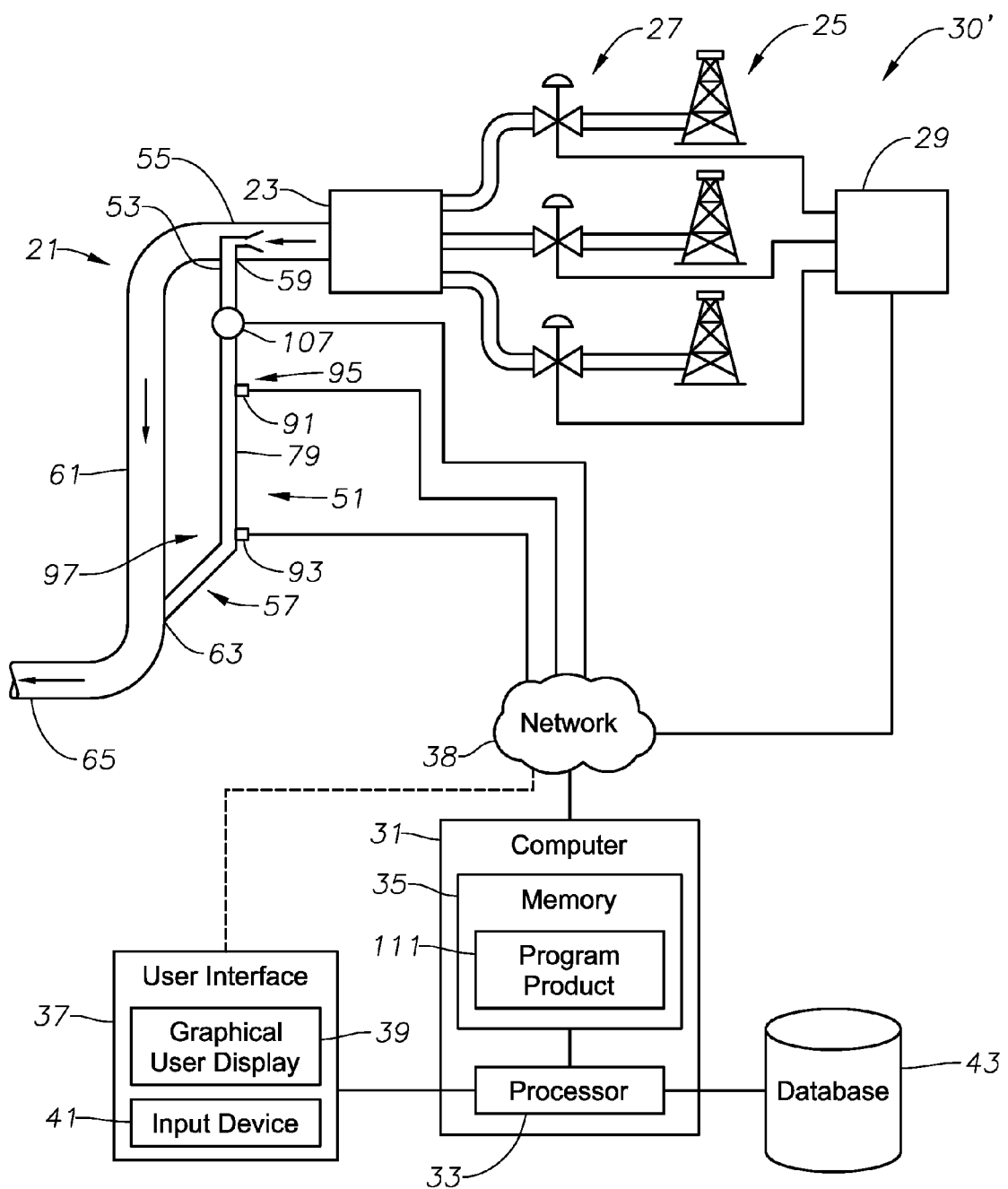
FIG. 2 is a schematic block diagram of a system to estimate and manage flowing fluid characteristics of fluid flowing through a pipeline according to an embodiment of the present invention.

More specifically, as perhaps best shown in FIGS. 1-2, embodiments of the present invention can include a system 30, 30', to estimate and manage flowing fluid characteristics of a fluid stream of fluid in the form of dehydrated degassed dead crude oil flowing through a pipeline 21 in or emanating from a processing facility 23 for transporting dehydrated degassed dead crude oil to a destination facility (not shown). The processing facility 23 receives wet gasified crude oil from and is in fluid communication with, a plurality of oil wells 25, each having a flow control device or valve 27 associated therewith and controlled by an engineering station 29. As will be described in more detail below, in the illustrated configuration, the flow control valves 27 are each in communication with a system computer or controller 31, manually or through automated systems via the engineering station 29, to control a flow rate of crude oil entering the processing facility 23, and thus, to control the flow rate and/or blend of the processed crude oil entering (and therefore exiting) the pipeline 21.

The wells 25 can have varying grades of crude oil resulting in the process crude oil processed by processing facility 23 having a complex crude blend. Particularly, although wells 25 from the same area tend to have similar grades, one or more of the wells 25 can have either an exceptionally high grade or an exceptionally low grade. Further, although all of the wells 25 may be producing a somewhat similar grade, one or more may be below a minimum threshold which, if not restricted, would result in the overall complex blend falling below some minimum threshold value.

As noted above, the system 30, 30', can include a fluid characteristics analysis and management controller or other form of computer 31. Such computer 31 can contain or otherwise include a processor 33, and memory 35 coupled to the processor 33 to store software and database records therein, for example, connected directly to system/non-system components (see, e.g., FIG. 1) and/or networked to such components (see, e.g., FIG. 2), Note, the computer 31 can be in the form of a personal computer or in the form of a server serving multiple user interfaces 37.

The system 30, 30', can also include a user interface 37 which can include a graphical display 39 for displaying graphical images, and a user input device 41 as known to those skilled in the art, to provide a user access to manipulate the software and database records. Accordingly, the user interface 37 can be either directly connected to the computer 31 or through a network 38, as known to those skilled in the art.

The system 30, 30', can further include a database 43 stored in the memory 35 (internal or external, networked, or non-networked) of the fluid characteristics analyzing computer 31 and having a various standard condition values, flow rate values, and other parameters, discussed below, utilized in analyzing and recording the fluid characteristics of the fluid flowing through pipeline 21, described in more detail below.

As perhaps best shown in FIGS. 1-4, the system 30, 30', can also include a bypass line 51 having a proximal end portion 53 connected to a horizontal section 55 of the pipeline 21 to receive a portion of the fluid stream flowing through the pipeline 21 (crude oil sample) and having a distal end portion 57 positioned to reintroduce the crude oil sample back into the fluid stream of the pipeline 21 once the analysis of the sample is completed. According to a preferred configuration, the section 55 of the pipeline 21 has an aperture 59 for communicating fluid to the bypass line 51. Correspondingly, an elongate vertical section 61 of the pipeline 21 also includes an aperture 63 for receiving sampled fluid from the bypass line 51. According to a preferred configuration, the aperture 63 is vertically located along a lower portion of the elongate vertical section 61, for example, adjacent to a horizontal section 65 of the pipeline 21. According to an embodiment of the system 30, 30', distal end portion 57 of the bypass line 51 need not extend through the outer wall surface 81 (see, e.g., FIG. 4) of the pipeline 21 and substantially into the flow stream to thereby minimize any fluid flow disruption during and after sampling. Further, the aperture 59 is preferably located on an underside (bottom) of the horizontal section 55 of the pipeline 21 to further minimize fluid flow disruption during sampling. Note, in an alternative configuration, the proximal end portion 53 of the bypass line 51 can be alternatively connected to an upper portion of the elongate section 61 and/or the distal end portion 57 of the bypass line 51 can be alternatively connected to the horizontal section 65 of the pipeline 21.

The proximal end portion 53 of the bypass line 51 can include a fluid collection extension 67 extending into the flow stream of section 55 of the pipeline 21. The fluid collector extension 67 can include a proximal end portion 69 extending radially from the aperture 59 and a distal end portion 71 having an axis substantially oriented parallel to the flow stream of section 55 to form, for example, an elbow-shaped fluid collection extension to thereby enhance gathering a fluid sample into the bypass line 51. The fluid collector extension 67 can include a conical flange 73 integral with or otherwise connected to the distal end portion 71. The flange 73 can include a fluid inlet aperture 75 also axially oriented with the flow stream of section 55 and having diameter larger than a diameter of the fluid inlet aperture 77 of the distal end portion 71 to thereby further enhance fluid sample collection into the bypass line 51.

The distal end portion 57 of the bypass line 51 extends acutely from a position just below a vertically oriented extent (main body portion) 79 of the bypass line 51 to aperture 63 extending through an outer surface 81 of the elongate vertical section 61, which is preferably located close to a lower (bottom) portion of the elongate vertical section 61 adjacent the horizontal section 65. According to a preferred configuration, the proximal end portion 53 and the main body portion 79 (located between the proximal end portion 53 and the distal end portion 57) both extend vertically downward from the section 55 of pipeline 21, and the distal end portion 57 extends, for example, between the main body portion 79 and the aperture 63 at an angle 83. Angle 83 is preferably less than approximately 45 degrees, but more preferably between approximately 15 degrees and 45 degrees, and still more preferably between approximately 20 degrees and 35 degrees, and even more preferably at approximately 25 degrees, to thereby enhance creation of a section mechanism into the bypass line 51, and thus, extraction of prior sampled fuel when a fresh sample is desired.

Figure 3:
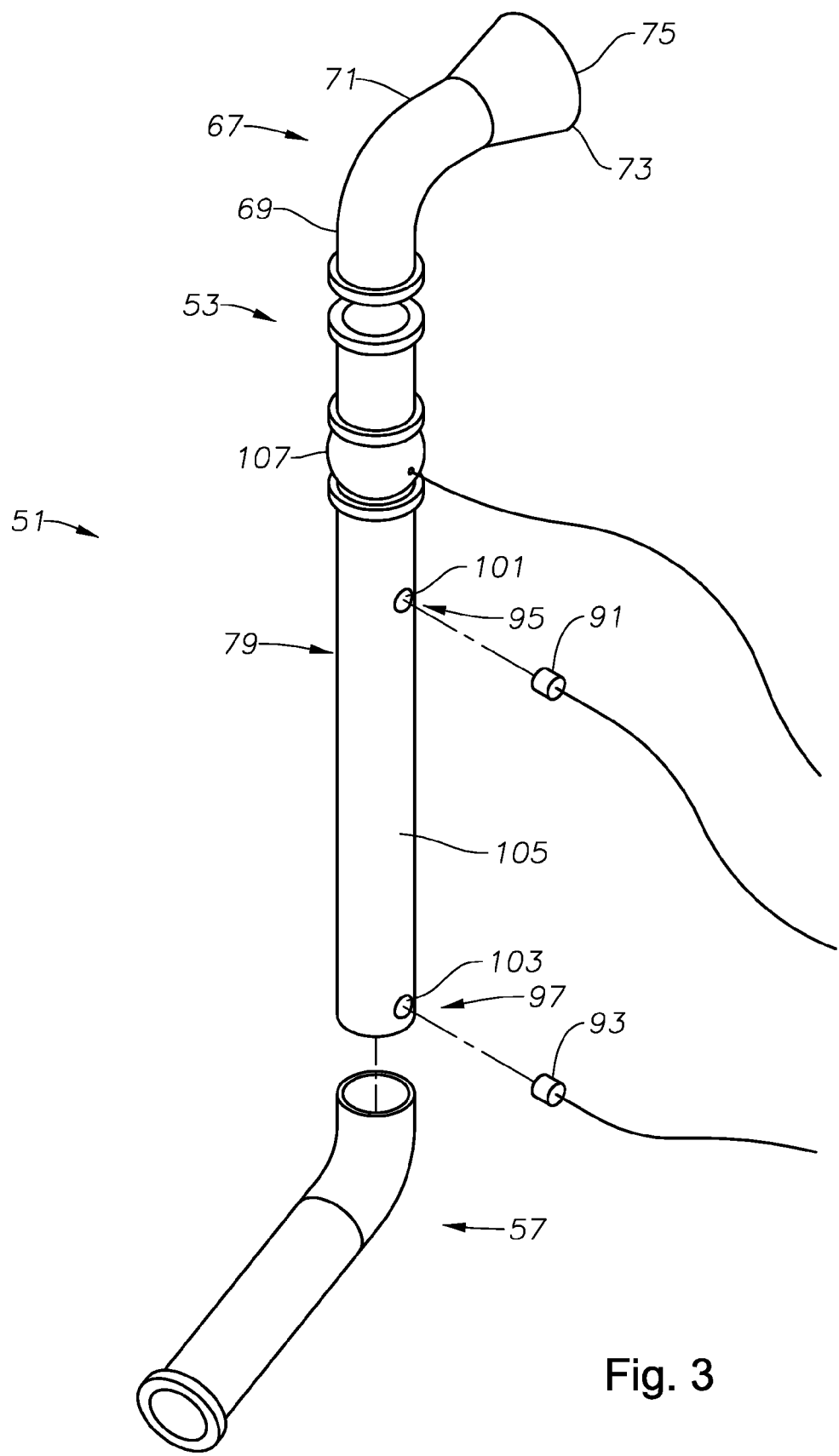
FIG. 3 is an exploded perspective view of a portion of a bypass line including a pressure and temperature sensor assembly and isolation valve according to an embodiment of the present invention.

As perhaps best shown in FIGS. 3-5, the bypass line 51 can include a pair of sensors/sensor assemblies 91, 93 connected along or to separate, spaced apart, portions or locations 95, 97, of the vertically oriented extent 79 of the bypass line 51 vertically oriented to some azimuth greater than zero degrees, but preferably at least approximately 45 degrees, and more preferably approximately 90 degrees (as illustrated), so that the sampled crude oil flowing through the vertically oriented extent 79 flows downward between the first location 95 and the second location 97 along the vertically oriented extent 79. As perhaps best shown in FIG. 4, in the exemplary configuration, the second location 97 can be substantially vertically spaced apart from and vertically below the first location 95, at a preselected elevation "h." The first sensor/sensor assembly 91 is positioned at the first location 95 to provide at least one signal indicative of pressure of the crude oil at the first location 95. The second sensor/sensor assembly 93 is positioned at the second location 97 to provide at least one signal indicative of pressure of the crude oil at the second location 97.

Note, the elevation "h" between sensors/sensor assemblies 91, 93, can vary depending upon the desired accuracy, but should generally be greater than approximately 10 feet, to overcome accuracy limitations of the pressure sensors/sensor assemblies 91, 93. Notably, the larger the elevation "h," the better the accuracy due to the provision of a larger sample. Nevertheless, due to wireline/wireless connectivity requirements, the elevation "h" is preferably between 20 feet and 100 feet, and more preferably between 25 feet and 35 feet. Note also, in configurations where the vertically oriented extent 79 of the bypass line 51 is not oriented normal to the earth's surface, the elevation "h" will not be the physical distance between respective locations 95, 97, where pressure readings are being taken, but rather the distance between two parallel planes each separately passing through the respective location 95, 97, where the respective pressure readings are being taken, and each perpendicular to the force of gravity.

According to a preferred configuration, the first sensor/sensor assembly 91 also provides the temperature of the crude oil at the first location 95. The second sensor/sensor assembly 93 is positioned at the second location 97 to provide at least one signal indicative of pressure of the crude oil at the second location 97. Similarly, according to the preferred configuration, the second sensor/sensor assembly 93 also provides the temperature of the crude oil at the second location 97. Particularly, sensor/sensor assemblies 91, 93, can each be a combined pressure-temperature transducer as known to those skilled in the art, each typically requiring only a single aperture 101, 103, extending through the outer surface 105 of the vertically oriented extent 79 of the bypass line 51 at their respective locations 95, 97, as perhaps best shown, for example, in FIG. 3. Note, however, the use of separate temperature transducers is within the scope of the present invention.

Further, according to various embodiments of the present invention, the spacing of the temperature transducers between each other at their respective locations 95, 97, need not be exact or substantially exact, although precision dictates preferably determining the respective first and second temperatures at the respective first and second locations 95, 97, at a same axial position as that of the first and the second pressure readings, respectively. That is, the temperatures should be taken at as close as possible to where the pressures are taken, or at least as close as possible to a same axial location along the vertically oriented extent 79 of the bypass line 51 as that of the first and the second pressures if separate temperature/pressure transducers or other sensors 91, 93, are utilized at the respective first and second locations 95, 97.

Still further, as shown in FIG. 3, at least portions of the first sensor/sensor assembly 91 can extend through a first pressure aperture or tap 101 in an outer wall surface 105 of the vertically oriented extent 79 of the bypass line 51 at the first location 95. Similarly, at least portions of the second sensor/sensor assembly 93 can extend through a second pressure aperture or tap 103 in the outer wall surface 105 of the vertically oriented extent 79 of the bypass line 51 at the second location 97. According to an embodiment of the system 30, 30', the crude oil extracted into the sample area of the vertically oriented extent 79 of the bypass line 51 is in fluid contact with at least portions of the first and the second pressure sensors/sensor assemblies 91, 93.

The sensors/sensor assemblies 91, 93, according to such embodiment of the system 30, 30', can also be strategically positioned, for example, through taps 101, 103 in the outer wall surface 105 of the vertically oriented extent 79 of the bypass line 51, to thereby negate a need for a fluid collection extension to be separately inserted into the bypass line 51 to interface the sampled fluid (e.g., crude oil) extracted from within the pipeline 21 with the sensors/sensor assemblies 91, 93, to thereby allow performance of the pressure and/or temperature analysis on the flowing fluid.

Further, as perhaps best shown in FIGS. 3-4, the sensors/sensor assemblies 91, 93, according to an embodiment of the system 30, 30', can also be strategically positioned along a vertically oriented extent (e.g., extent 79) at separate elevations (e.g., separated by elevation h), and the bypass line 51 can be connected at least partially across a vertically oriented extent (e.g., extent 61) of the pipeline 21 to thereby negate a need for a fluid sampling pump (not shown) to extract the fluid within the pipeline 21 for pressure and/or temperature analysis. That is, rather than requiring utilization of a fluid sampling pump, such embodiment of the system 30, 30', beneficially utilizes gravity to establish a pressure differential between sensors/sensor assemblies 91, 93, reducing the complication of excess mechanical components needed to interface with the pipeline 21 and the amount and cost of components needed to perform an initial installation or a retrofit of an existing pipeline 21. Beneficially, for a retrofit, managers need only select a portion of the pipeline 21 for inclusion of pipeline taps 59, 63, either pre-pipeline deployment or post-pipeline deployment, if such taps 59, 63, do not already exist, to allow interface with the bypass line 51 which carries the necessary sensors/sensor assemblies 91, 93, etc.

Although analyzing pressure readings of fluid flowing through the bypass line 51, when flowing, is within the scope of the present invention, according to a preferred configuration, the system 30, 30', can also include a remotely operated valve 107 interfaced with the bypass line 51 positioned, for example, downstream of the connection of the proximal end portion 53 of the bypass line 51 to the pipeline 21 (e.g., downstream of aperture 59), and upstream of the first location 95 along the extent 79 of the bypass line 51 (e.g., upstream of sensor/sensor assembly 91). Functionally, the remotely operated valve 107 can include an isolation solenoid valve configured to segment the flow through the bypass line 51 at specific intervals, or on demand, in order to take static fluid flow readings of the otherwise dynamic fluid flow.

The system 30, 30', can include crude oil analysis and management program product 111 stored in memory 35 of the fluid characteristics analysis and management computer 31. The program product 111, according to an embodiment of the system 30, 30', is adapted: to receive pressure and/or temperature inputs, to provide estimates of various flowing fluid characteristics including, for example, one or more of the following: an estimated density of the flowing fluid (e.g., crude oil) flowing through the pipeline 21, an estimated specific gravity of the flowing fluid, and an estimated API gravity of the flowing fluid, etc. Note, the crude oil analysis and management program product 111 can be in the form of microcode, programs, routines, and symbolic languages that provide a specific set for sets of ordered operations that control the functioning of the hardware and direct its operation, as known and understood by those skilled in the art. Note also, the crude oil analysis and management program product 111, according to an embodiment of the present invention, need not reside in its entirety in volatile memory, but can be selectively loaded, as necessary, according to various methodologies as known and understood by those skilled in the art of computer systems.

Figure 6:
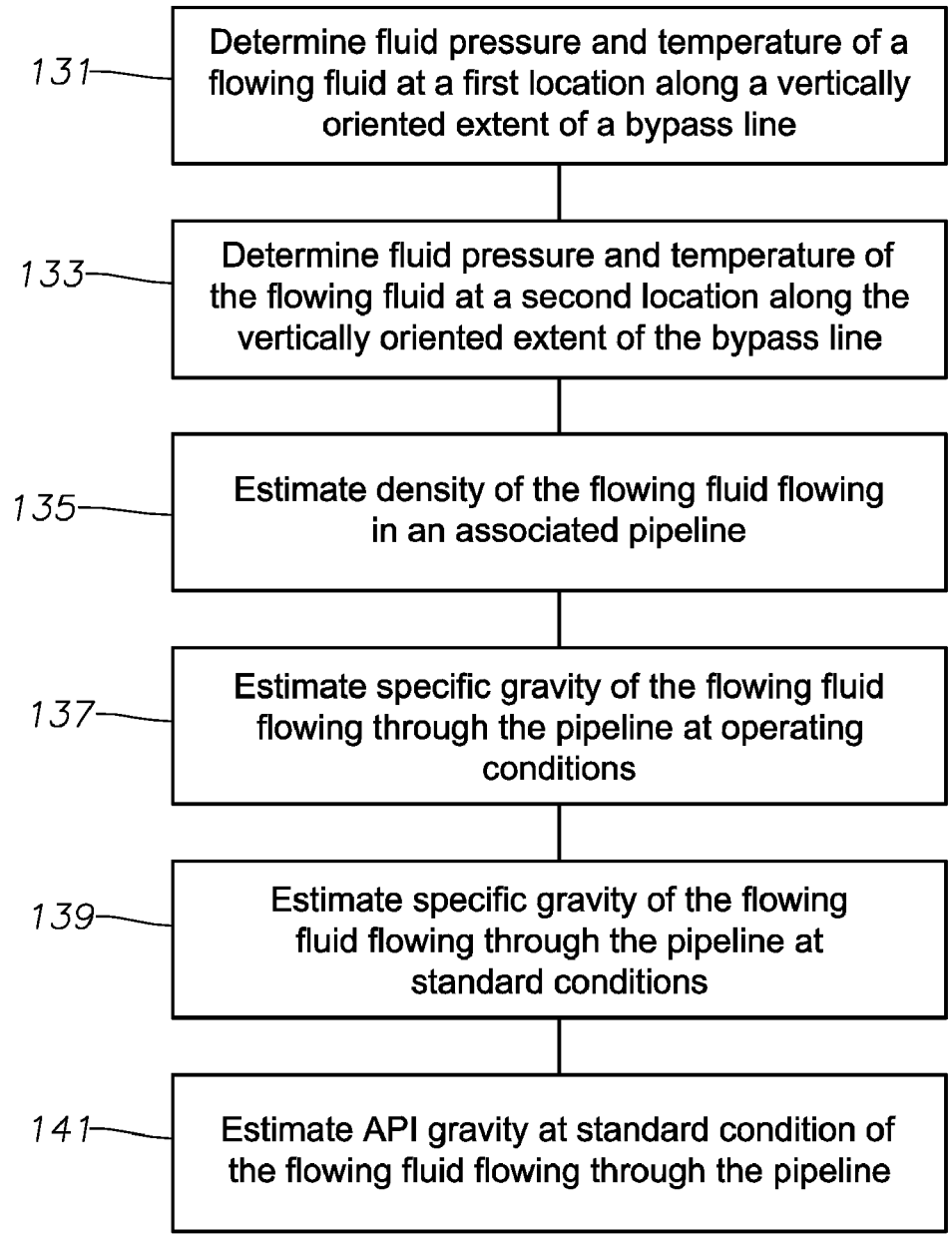
FIG. 6 is a schematic flow diagram of a method and operations for estimating and managing flowing fluid characteristics of a fluid flowing through a pipeline according to an embodiment of the present invention.

FIG. 6 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, at operating and standard conditions. According to the illustrated embodiment of the present invention, the method can include the steps of determining fluid pressure and temperature of the crude oil sample at a first location 95 (e.g., proximal or upper end portion along a vertically oriented extent 79) of the bypass line 51 carrying a sample of the crude oil, for example, flowing or approaching to flow downward through an adjacent vertically oriented extent 61 of the pipeline 21 (block 131); and determining fluid pressure and temperature of the crude oil sample at a second location 97 (e.g., distal or lower end portion along a vertically oriented extent 79) substantially vertically spaced apart from the first location 95 along the vertically oriented extent 79 and vertically below the first location 95 (block 133). The bypass line 51, in conjunction with the remotely operated valve 107, can function to extract and isolate the crude oil sample for analysis. According to an exemplary configuration illustrated in FIG. 3, the fluid pressure and temperature at the first location 95 can be determined using a first transducer 91 coupled to a first fluid tap 101 either pre installed or drilled through an outer surface 105 of the vertically oriented extent 79. The fluid pressure and temperature at the second location 97 can be determined using a second transducer 93 coupled to a second fluid tap 103. The first and the second pressure and/or temperature taps 101, 103, can be installed such that when the vertically oriented extent 79 of the bypass line 51 is operationally inserted, installed, or otherwise interfaced with the pipeline 21, the taps 101, 103, have a predetermined or otherwise preselected vertical elevation therebetween, shown as elevation "h" in FIG. 4. Note, according to a preferred installation arrangement, when operatively installed, the first and the second transducers (or other sensors/sensor assemblies) 91, 93, are extended into or through the taps 101, 103, sufficiently to obtain a robust reading, but without substantially impeding fluid flow of the crude oil in the bypass line 51 when the remotely operated valve 107 is opened to obtain a fresh crude oil sample, or causing a substantial amount of turbulence due to an impacted surface area of the sensors 91, 93, when impacted or otherwise in free contact with the flowing fluid.

The method can also include the step of estimating API gravity at standard condition of the crude oil, for example, flowing or approaching to flow through the vertically oriented extent 81 of the pipeline 21 (block 141), for example, either directly responsive to: the determined fluid pressure and temperature at the first location 95 along the vertically oriented extent 79 of the bypass line 51, the determined fluid pressure and temperature at the second location 97, and vertical elevation "h" between, for example, the pressure sensing portions of the sensors/sensor assemblies 91, 93; or indirectly by first solving for: the density (block 135), specific gravity at operating conditions (block 137), and/or specific gravity at standard conditions (block 139) of the crude oil flowing through the pipeline 21.

According to an embodiment of the method, the API gravity at standard condition can be estimated using the following calculations:

$$\rho_c = \frac{P_2 - P_1}{h};$$

$$\gamma = \frac{\rho_c}{\rho_w};$$

$$\text{Crude } API = \left(\frac{141.5}{\gamma} - 131.5\right);$$

$$\gamma_{STD} = \gamma[1 - \beta(T_2 - T_1)];$$

$$\text{Crude } API_{STD} = \left(\frac{141.5}{\gamma_{STD}} - 131.5\right);$$

where:
$\rho_c$ is the density of the crude oil,
$P_1$ is the determined fluid pressure at the first location,
$P_2$ is the determined fluid pressure at the second location,
h is the vertical elevation between the first and the second fluid pressure taps/sensors in the vertically oriented extent of the bypass line,
$\gamma$ is the specific gravity of the crude oil at operating condition,
$\rho_w$ is the density of water: 62.4 lb/ft$^3$,
API is the API at current operating conditions,
$\gamma_{STD}$ is the specific gravity of the crude oil at standard condition,
$\beta$ is the coefficient of isobaric thermal expansion,
$T_1$ is the determined fluid temperature at the first location,
$T_2$ is the determined fluid temperature at the second location, and
$API_{STD}$ is the API at current standard conditions.

Notably, if the pressure and temperature readings are taken with the remotely operated valve 107 opened (e.g. fluid in a dynamic state), rather than with the remotely operated valve 107 closed (e.g., fluid in a static state), a correction factor CF that accounts for frictional pressure loss between the first and the second locations 95, 97, should be applied to the density estimation to enhance accuracy.

Figure 7:
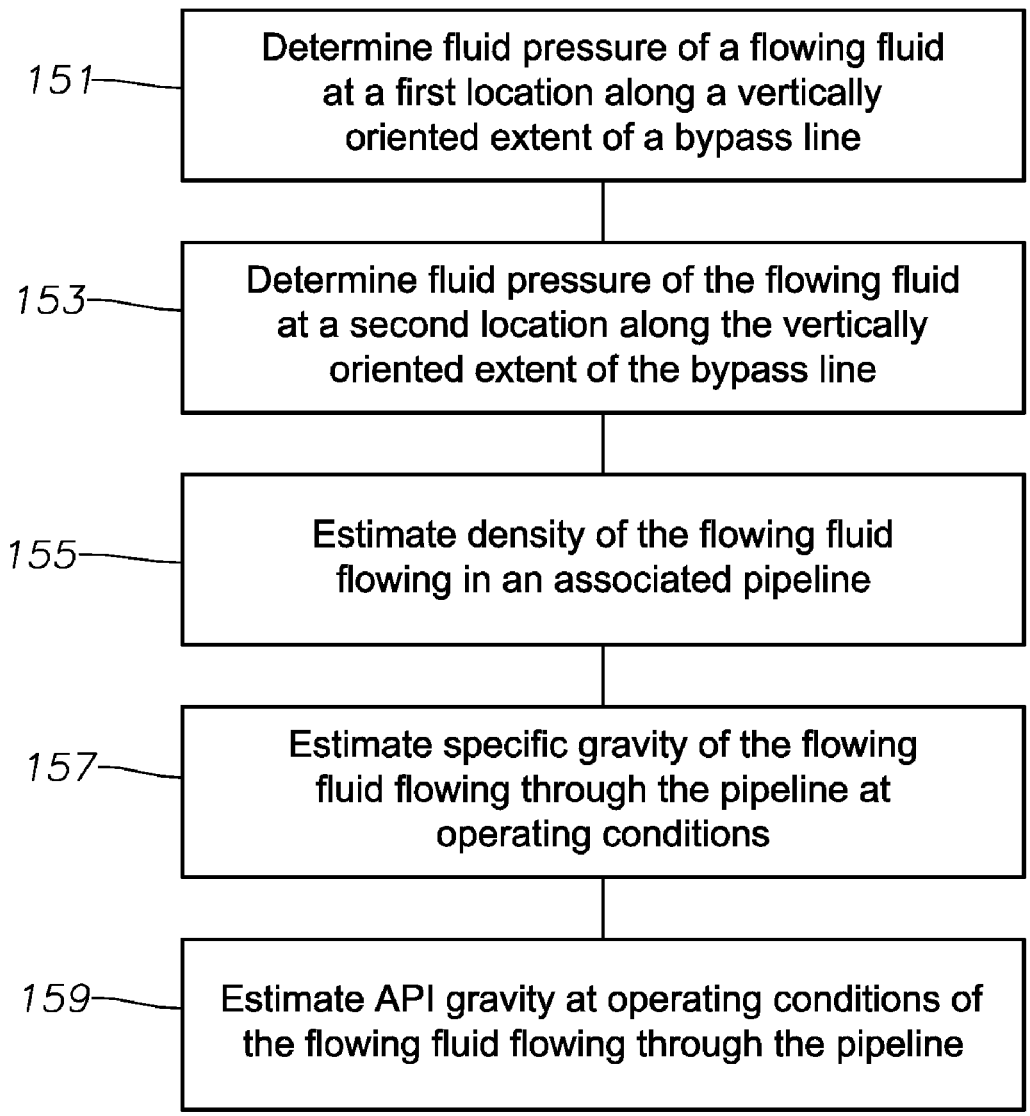
FIG. 7 is a schematic flow diagram of a method and operations for estimating and managing flowing fluid characteristics of a fluid flowing through a pipeline according to an embodiment of the present invention.

FIG. 7 provides a high-level flow diagram illustrating a method for estimating and managing flowing fluid characteristics of a fluid stream (e.g., dehydrated and/or degassed crude oil) flowing through a pipeline (e.g., pipeline 21), for example, in a processing facility (e.g., process facility 23), in real-time, at operating conditions, rather than standard conditions. According to an embodiment of the method, the method can include the steps of determining fluid pressure of the crude oil at a first location 95 (e.g., proximal or upper end portion along a vertically oriented extent 79) of the bypass line 51 (block 151) which, in conjunction with the remotely operated valve 107, can function to extract and isolate the crude oil sample. When the remotely operated valve 107 is opened, the fluid which can be isolated to form the sample flows downward between the first location 95 and a second location 97 (e.g., distal or lower end portion along a vertically oriented extent 79) substantially vertically spaced apart from the first location 95 along the vertically oriented extent 79 and vertically below the first location 95. When at least a sufficient fluid is extracted from the main fluid flow to "flush" the prior sample from within the bypass line 51, e.g., using a preselected time delay, the valve 107 is then closed to isolate the current sample—thus, producing static fluid conditions for the sample. The pressure associated with the main fluid flow adjacent the proximal end portion 53 of the bypass line 51 is applied via aperture 63 to the sample. The pressure associated with the main fluid flow adjacent the distal end portion 57 of the bypass line 51 is applied to the sample via aperture 63. Accordingly, the method also includes determining fluid pressure of the crude oil at the second location 57 along the vertically oriented extent 79 of the bypass line 57 (block 153). The method can also include the step of estimating API gravity at operating condition of the crude oil flowing through the vertically oriented extent 61 of the pipeline 21 (block 159), for example, either directly responsive to the determined fluid pressure at the first location 95, the determined fluid pressure at the second location 97, and vertical elevation "h" between the sensors 91, 93, or indirectly by first solving for the density (block 155) and specific gravity (block 157) of the crude oil flowing through the pipeline 21. Further, the method and operations can alternatively include individually solving for density or specific gravity, particularly where API gravity is not required.

FIGS. 4 and 5 provide an example of an implementation including exemplary numerical values (see FIG. 4) according to the embodiment of the method illustrated in FIG. 7. According to the exemplary implementation shown in FIG. 4, the remotely operated valve 107 is opened to a lower a portion of a flow stream of completely degassed crude oil flowing in pipeline 21 (typically with a known flow rate) to be extracted into bypass line 51. As shown in FIG. 5, the remotely operated valve is closed to isolate the crude oil sample. In this example, the vertical distance between the two pressure sensors 91, 93, in the vertically oriented extent 79 of the bypass line 51 is 30 feet, the upper pressure reading is 189.7 psig, and the lower pressure reading is 200.8 psig. Under such static conditions, the pressure differential is due to gravity, with no correction factor needed to account for frictional pressure losses, as would be the case if the fluid within the bypass line 51 were flowing when the pressure readings were taken. Using these pressure readings, the following calculations can then be performed, for example, to determine density, specific gravity, and/or API gravity:

$$CrudeDensity(\rho_c) = \frac{200.8 - 189.7}{30 * 12}$$

$$= 0.03083 \frac{lb}{in^3} * \frac{1728 \, in^3}{ft^3}$$

$$= 53.28 \frac{lb}{ft^3}$$

$$Specific \, Gravity(\gamma) = \frac{53.28}{62.4} = 0.8539$$

$$Crude \, API = \left[\frac{141.5}{0.8539} - 131.5\right] = 34.2° \, API$$

This value for the crude API gravity can then readily be corrected for temperature at the two sensor locations, if desired.

Figure 8:
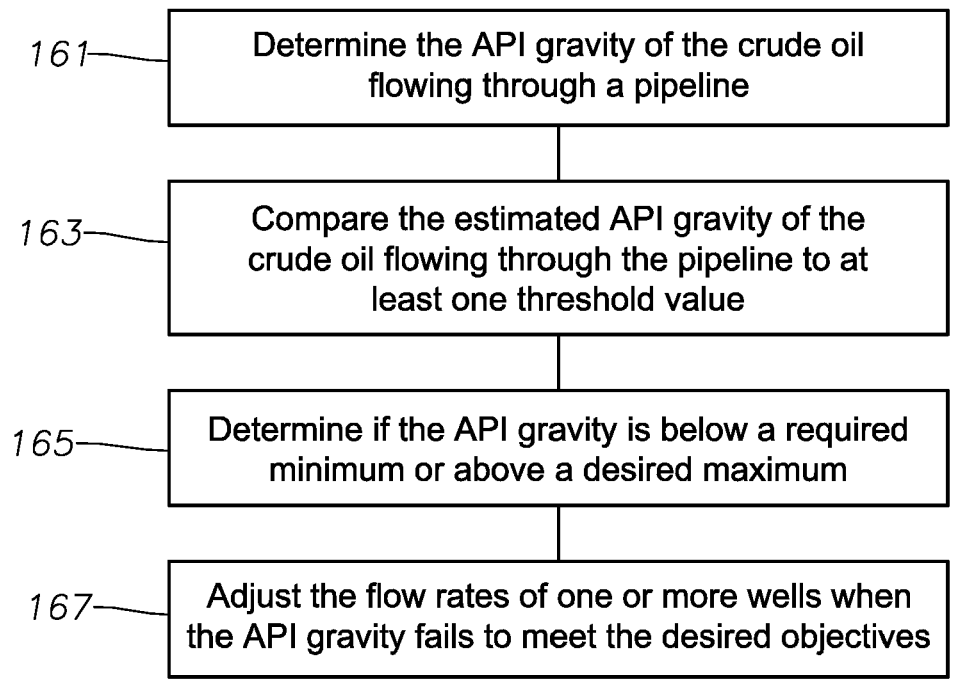
FIG. 8 is a schematic flow diagram of a method and operations for estimating and managing flowing fluid characteristics of a fluid flowing through a pipeline according to an embodiment of the present invention.

FIG. 8 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, which includes application of the determined API gravity fluid stream to control the blend (grade) of the crude oil flowing through the pipeline 21. The method can include first determining the density, specific gravity, and/or API gravity, either under operating conditions or standard conditions. Specifically, according to an embodiment of the method, the crude oil includes a complex crude blend including a plurality of crude grades, for example, emanating from a plurality of oil wells (e.g., wells 25) in fluid communication with the processing facility 23 and controlled by a corresponding plurality of flow control valves (e.g., control valves 27). Accordingly, in a preferred embodiment of the method, the method can include determining the API gravity of the complex blend of crude oil flowing through the pipeline 21 (block 161), for example, using the process steps described previously; comparing the estimated API gravity of the crude oil flowing through the pipeline 21 to at least one threshold value (block 163) to determine if the API gravity has failed to meet the at least one threshold value (i.e., if it is below a required minimum or above a desired maximum) to thereby maintain the API gravity above a preselected desired minimum value or within a preselected desired range limit (block 165); and adjusting the flow rates of one or more of the plurality of wells 25 responsive to determining that the API gravity fails to meet the at least one threshold value (block 167) to thereby meet or maintain crude oil grade objectives.

Figure 9:
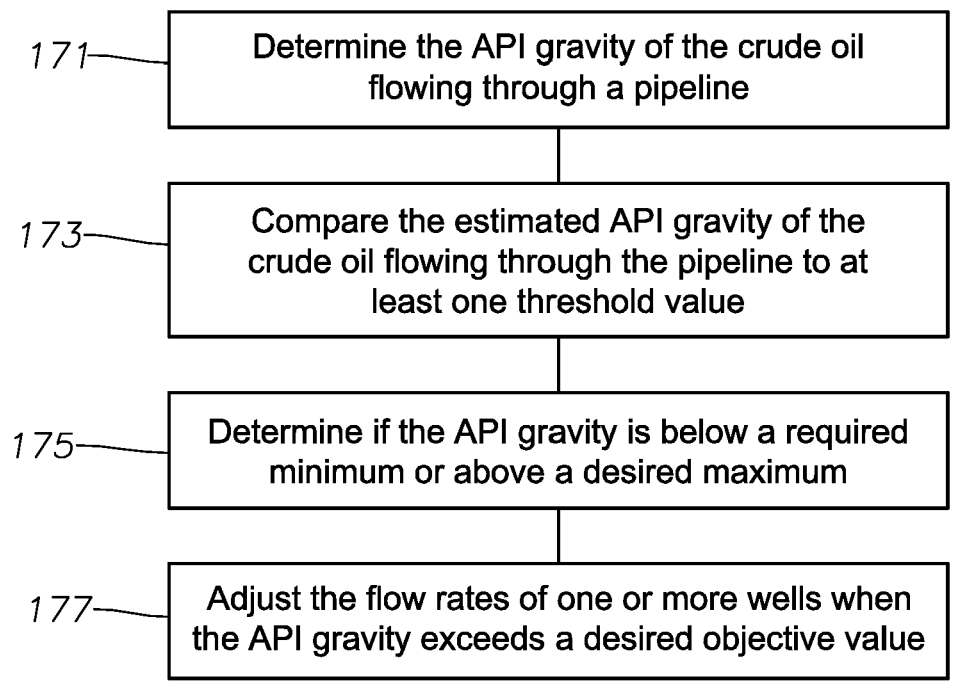
FIG. 9 is a schematic flow diagram of a method and operations for estimating and managing flowing fluid characteristics of a fluid flowing through a pipeline according to an embodiment of the present invention.

FIG. 9 provides a high-level flow diagram illustrating a method (and operations) for estimating and managing flowing fluid characteristics of a fluid stream (e.g., dehydrated and/or degassed crude oil) flowing through a pipeline (e.g., pipeline 21), for example, in a processing facility (e.g., process facility 23) in real-time, which includes application of the determined API gravity to control the blend (grade) of the crude oil flowing through the pipeline 21, according to another preferred configuration. According to such embodiment of a method, the method can include determining the API gravity of the crude oil flowing through the pipeline 21 (block 171), for example, using the process steps described previously; comparing the estimated API gravity of the crude oil flowing through the pipeline 21 to at least one threshold value (block 173) to determine if the API gravity has exceeded the at least one threshold value (i.e., if it is below a required minimum or above a desired maximum) to thereby maintain the API gravity within a preselected desired range limit (block 175); and when exceeding such threshold value or values, adjusting the flow rates of one or more of the wells 25 (block 177) to thereby meet or maintain crude oil grade objectives.

Notably, according to an exemplary implementation, production from a high-grade well 25 could be increased if the complex grade was determined to be insufficient, and production from a corresponding one or more wells 25 with a lower grade (typically a grade above or very close to the threshold), could be reduced a corresponding amount to maintain the overall flow rate of the crude oil flowing through pipeline 21. According to such implementation, production of a subpar well or wells 25 could be continued until such time that it is decided to rework or abandon the subpar well 25.

Figure 10:
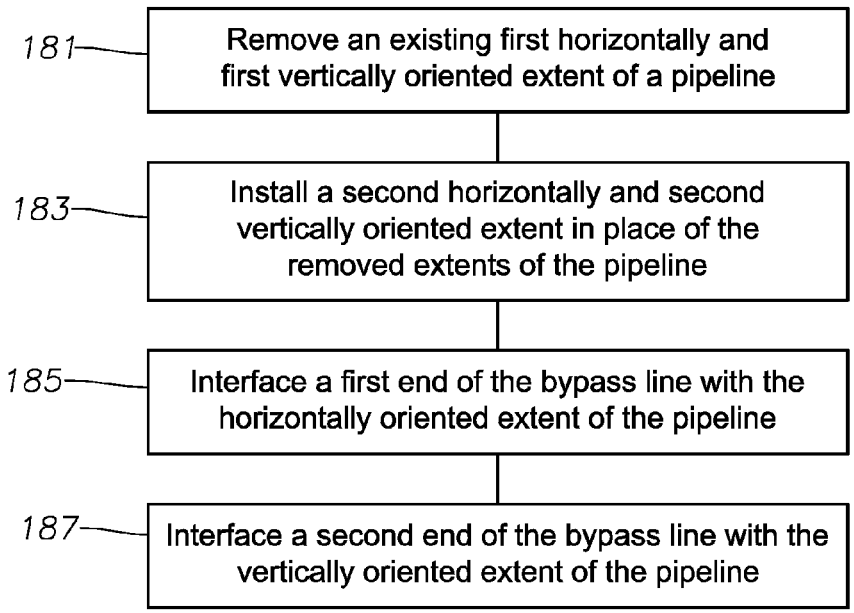
FIG. 10 is a schematic flow diagram of a method of retrofitting a portion of a pipeline with a bypass line according to an embodiment of the present invention.

FIG. 10 provides a high-level flow diagram illustrating preliminary steps regarding application of, e.g., the bypass line 51 (e.g., including remotely operated valve 107 and sensors/sensor assemblies 91, 93), which can be utilized in order to implement the various embodiments of the methods and operations for estimating and managing flowing fluid characteristics of a fluid stream, as described above. According to an embodiment of such method, the method can include the steps of removing an existing a first horizontally oriented extent 55 and a first vertically oriented extent 61 of the pipeline 21 (block 181), and installing a second horizontally oriented extent 55 and a second vertically oriented extent 61 in place of the removed first horizontally oriented extent 55 and first vertically oriented extent 61 of the pipeline 21 (block 183). According to the illustrated embodiment of the present invention, as perhaps best shown in FIGS. 4 and 5, the second horizontally oriented extent 55 includes an aperture 59 and the vertically oriented extent 61 includes an aperture 63 extending through the outer wall surface 89 of the pipeline 21. The method can also include connecting or otherwise interfacing a first or proximal end 53 of the bypass line 51 with the horizontally oriented extent 55 of the pipeline 21 (block 185) to allow the bypass line 51 to receive a fluid sample of fluid flowing through pipeline 21 via aperture 59; and connecting or otherwise interfacing a second or distal end 57 of the bypass line 51 with the vertically oriented extent 61 of the pipeline 21 (block 187) to reintroduce the sampled fluid back into the mainstream fluid flow after pressure/temperature analysis of the sample is completed. Note, according to an alternative embodiment of the method, both apertures 59 and 63 can be located in the vertically oriented extent 61, negating any need for replacing the horizontally oriented extent 55.

Figure 11:
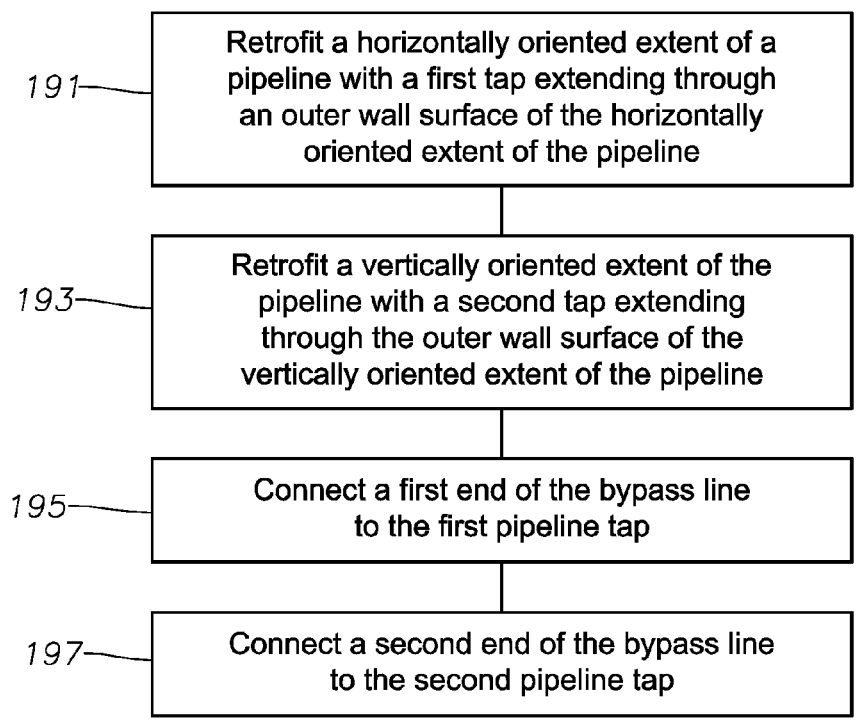
FIG. 11 is a schematic flow diagram of a method of retrofitting a portion of a pipeline with a bypass line according to an embodiment of the present invention.

FIG. 11 provides a high-level flow diagram illustrating preliminary steps regarding application of, e.g., the bypass line 51 (e.g., including remotely operated valve 107 and sensors/sensor assemblies 91, 93), which can be utilized in order to implement the various embodiment of the methods and operations for estimating and managing flowing fluid characteristics of a fluid stream, as described above, according to another embodiment of the present invention. The method can include retrofitting a horizontally oriented extent 55 of the pipeline 21 with a first aperture 59 adjacent a vertically oriented extent 61 to define a first pipeline tap 59 extending through the outer wall surface 89 of the pipeline 21 (block 191), retrofitting the vertically oriented extent 61 of the pipeline 21 with a second aperture 63 to define a second pipeline tap 63 extending through the outer wall surface 89 of the vertically oriented extent 61 of the pipeline 21 (block 193), connecting the proximal end portion 53 of the bypass line 51 (first end) to the first pipeline tap 59 (block 195), and connecting the distal end portion 57 of the bypass line 51 (second end) to the second pipeline tap 63 (block 197). Note, according to an alternative embodiment of the method, the vertically oriented extent 61 of the pipeline 21, alone, can instead be retrofitted with both apertures 59 and 63, negating any need for performing any retrofit operations on the horizontally oriented extent 55.

It is important to note that while the foregoing embodiments of the present invention have been described in the context of a fully functional system and process, those skilled in the art will appreciate that the mechanism of at least portions of the present invention and/or aspects thereof are capable of being distributed in the form of a computer readable medium storing a set of instructions in a variety of forms for execution on a processor, processors, or the like, and that embodiments of the present invention apply equally regardless of the particular type of signal bearing media used to actually carry out the distribution. Examples of computer readable media include, but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD -R/RWs, DVD-RAMs, DVD-R/RWs, DVD+R/RWs, flash drives, and other newer types of memories, and transmission type media such as digital and analog communication links Capable of storing the set of instructions. Such media can include, for example, both operating instructions and operations instructions described with respect to program product 111, the program product 111, itself, and the computer executable portions of the method steps according to the various embodiments of a method of estimating and managing flowing fluid characteristics of the fluid stream flowing through a pipeline, described above.

According to an embodiment of the computer readable medium and/or crude oil analysis and management program product 111 positioned thereon, such computer readable medium can include instructions that when executed by a processor, controller, or other form of computer (e.g., computer 31), cause the computer to perform the operations of providing a control signal to instruct a remotely operated valve (e.g., valve 107) to open to supply a crude oil sample of dehydrated degassed crude oil to a bypass line 51 positioned along or otherwise adjacent a vertically oriented extent 61 of a pipeline 21, providing a control signal to close the remotely operated valve 107 to substantially isolate the crude oil sample, receiving a signal/signals indicative of fluid pressure and temperature of the crude oil at a first location 95 from a sensor/sensor assembly 91 positioned along a vertically oriented extent 79 of the bypass line 51, receiving a signal/signals indicative of fluid pressure and temperature of the crude oil at a second location 97 from a sensor/sensor assembly 93 positioned along the vertically oriented extent 79 of the bypass line 51. The operations also include determining fluid pressure and temperature of the crude oil at the first location 95 responsive to the signal/signals provided by the first sensor/sensor assembly 91, determining fluid pressure and temperature of the crude oil at the second location 97 responsive to the signal/signals provided by the second sensor/sensor assembly 93, and estimating density, specific gravity, and/or API gravity of the crude oil flowing through the pipeline 21.

Particularly, the operations can include estimating density of the crude oil flowing through the pipeline 21 responsive to the determined fluid pressure at the first location 95, the determined fluid pressure at the second location 97, and the vertical elevation "h" between a pressure sensor portion of the first sensor/sensor assembly 91 and a pressure sensing portion of the second sensor/sensor assembly 93.

The operations can also include estimating specific gravity of the crude oil flowing through the pipeline 21, for example, at standard conditions, responsive to: the estimated density of the crude oil, determined fluid temperature at the first location 95, and the determined fluid temperature at the second location 95, the density of water, and estimated thermal expansion (e.g., via a coefficient of isobaric thermal expansion); and/or estimating API gravity of the crude oil flowing through the pipeline 21, for example, at standard conditions, responsive to the estimated specific gravity of the crude oil flowing through the pipeline 21.

The operations can further include comparing the estimated API gravity of the crude oil flowing through the pipeline 21 to at least one threshold value to determine if the API gravity has either failed to meet or exceeds the at least one threshold value to thereby maintain the API gravity above a preselected desired minimum value or within a preselected desired range limit, and adjusting the flow rate of one or more wells 25 responsive to determining that the API gravity fails to meet or exceeds the at least one threshold value (i.e., is below a required minimum or above a desired maximum). The operations can further include those which implement the above described method steps.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, although the description primarily focuses on crude oil, and more specifically, dehydrated degassed crude oil, one skilled in the art would recognize that embodiments of the present invention can be applied to any liquid fluid.

That claimed is:

1. A method for estimating and managing flowing fluid characteristics of a fluid stream flowing through a pipeline in a processing facility in real-time, the method comprising the steps of:

opening a remotely operated valve to supply a crude oil sample of dehydrated degassed crude oil to a vertically oriented bypass line, the bypass line having a proximal end portion connected to a section of a crude oil pipeline to receive a portion of the fluid stream flowing through the pipeline defining the crude oil sample and having a distal end portion positioned to reintroduce the crude oil sample back into the fluid stream of the pipeline, the crude oil sample flowing downward between a first location and a second location substantially vertically spaced apart from the first location along a vertically oriented extent of the bypass line and located vertically below the first location;

closing the remotely operated valve to substantially isolate the crude oil sample;

determining fluid pressure and temperature of the crude oil sample at the first location along the vertically oriented extent of the bypass line, the fluid pressure at the first location determined using a first pressure transducer coupled to a first bypass line fluid pressure tap in the bypass line;

determining fluid pressure and temperature of the crude oil sample at the second location along the vertically oriented extent of the bypass line, the fluid pressure at the second location determined using a second pressure transducer coupled to a second bypass line fluid pressure tap in the bypass line, the first and the second bypass line pressure taps having a predetermined vertical elevation therebetween:

estimating specific gravity of the crude oil flowing through the pipeline responsive to: the determined fluid pressure at the first location, the determined fluid pressure at the second location, and the vertical elevation between the first location and the second location; and estimating API gravity of the crude oil flowing through the pipeline at standard condition responsive to: the estimated specific gravity of the crude oil flowing through the pipeline, the determined fluid temperature at the first location, and the determined fluid temperature at the second location.

2. A method as defined in claim 1, wherein the estimated API gravity is estimated according to the following calculations:

$$\rho_c = \frac{P_2 - P_1}{h};$$

$$\gamma = \frac{\rho_c}{\rho_w};$$

$$\gamma_{STD} = \gamma[1 - \beta(T_2 - T_1)];$$

$$\text{Crude } API_{STD} = \left(\frac{141.5}{\gamma_{STD}} - 131.5\right); \text{ and}$$

wherein:
- $\rho_c$ is the density of the crude oil,
- $P_1$ is the determined fluid pressure at the first location,
- $P_2$ is the determined fluid pressure at the second location,
- $h$ is the vertical elevation between the first and the second bypass line fluid pressure taps,
- $\gamma$ is the specific gravity of the crude oil at operating condition,
- $\rho_w$ is the density of water,
- $\gamma_{STD}$ is the specific gravity of the crude oil at standard condition,
- $\beta$ is the coefficient of isobaric thermal expansion,
- $T_1$ is the determined fluid temperature at the first location, and
- $T_2$ is the determined fluid temperature at the second location.

3. A method as defined in claim 1, wherein the section of the crude oil pipeline is a preselected section of an existing pipeline located at a processing facility which connects to a vertically oriented extent of the pipeline, the method further comprising the steps of connecting the proximal end portion of the bypass line to the preselected section of the pipeline at a first pipeline tap and connecting the distal end portion of the bypass line to a distal portion of the vertically oriented extent of the pipeline at a second pipeline tap, to thereby retrofit the existing pipeline with the bypass line.

4. A method as defined in claim 3, further comprising the step of:

gathering the crude oil sample when the remotely operated valve is opened using a fluid collection extension extending into the fluid stream flowing in the preselected section of the existing pipeline;

wherein the fluid collection extension includes a conical flange having an inlet oriented substantially parallel with the fluid stream; and wherein the distal end portion of the bypass line is connected to the distal end portion of the vertically oriented extent of the pipeline at an angle of between approximately 15 degrees and 45 degrees.

5. A method as defined in claim 1, wherein the remotely operated valve is located downstream of the proximal end portion connection of the bypass line to the crude oil pipeline and upstream of the first location along the vertically oriented extent of the bypass line, the method further comprising the steps of:

periodically opening and closing the remotely operated valve to iteratively supply a new sample of dehydrated degassed crude oil to the bypass line to thereby estimate and manage the API gravity of the crude oil flowing through the pipeline in real-time.

6. A method as defined in claim 1, wherein the crude oil flowing through the pipeline comprises a mixture of a plurality of specific crude oil grades defining a complex crude oil blend received from a processing facility and provided to the processing facility by a plurality of oil wells each producing one of the plurality of crude oil grades, the method further comprising the steps of:

comparing the estimated API gravity of the crude oil flowing through the vertically oriented extent of the bypass line to at least one threshold value to determine if the API gravity has failed to meet the at least one threshold value; and adjusting the API gravity by adjusting a flow rate of one or more of the plurality of wells responsive to determining that the API gravity fails to meet the at least one threshold value to thereby maintain the API gravity above a preselected desired minimum value or within a preselected desired range limit.

7. A method as defined in claim 1, wherein the crude oil flowing through the pipeline comprises a mixture of a plurality of specific crude oil grades defining a complex crude oil blend received from a processing facility and provided to the processing facility by a plurality of oil wells each producing one of the plurality of crude oil grades, the method further comprising:

comparing the estimated API gravity of the crude oil flowing through the vertically oriented extent of the bypass line to at least one threshold value to determine if the API gravity has exceeded the at least one threshold value; and adjusting the API gravity by adjusting a flow rate of one or more of the plurality of wells responsive to determining that the API gravity exceeds the at least one threshold value to thereby maintain the API gravity within a preselected desired range limit.

8. A method as defined in claim 1, wherein the vertical elevation between the first and the second bypass line pressure taps is at least approximately 10 feet; and wherein an outer surface wall of the vertically oriented extent of the bypass line associated with the first location and an outer surface wall of the vertically oriented extent of the bypass line associated with the second location each extend circumferentially around a common longitudinal axis.

9. A method as defined in claim 1, wherein the pipeline is a primary crude oil pipeline having a dynamic flowstream; and wherein the bypass line is interfaced with a pair of vertically spaced apart pipeline fluid taps located on or adjacent a vertically oriented extent of the pipeline, and the first and the second pressure transducers are positioned along the vertically oriented extent of the bypass line, to thereby negate a need for a fluid sampling pump to extract the crude oil sample.

10. A method as defined in claim 1, wherein the pipeline is an existing flowline associated with a processing facility, the method further comprising the step of:
retrofitting the pipeline with the bypass line by interfacing the bypass line with or positioning the bypass line across a vertically oriented extent of the pipeline.

11. A method for estimating and managing flowing fluid characteristics of a fluid stream flowing through a pipeline in real-time, the method comprising the steps of:
determining fluid pressure of crude oil at a first location along a vertically oriented extent of a bypass line carrying a sample of crude oil extracted from a fluid stream flowing through a crude oil pipeline, the bypass line having a proximal end portion connected to the pipeline to receive a portion of the fluid stream flowing through the pipeline defining the crude oil sample and having a distal end portion positioned to reintroduce the crude oil sample back into the fluid stream of the pipeline, the fluid pressure at the first location determined using a first pressure sensor at least partially extending through a first portion of an outer wall surface of the bypass line;
determining fluid pressure at a second location along the vertically oriented extent of the bypass line, the fluid pressure at the second location determined using a second pressure sensor at least partially extending through a second portion of the outer wall surface of the bypass line at the second location, the first and second portions of the outer wall surface of the bypass line having a predetermined vertical elevation therebetween, the second portion of the outer wall surface of the bypass line positioned below the first portion of the outer wall surface when the bypass line is operably connected to the pipeline; and
estimating API gravity of the crude oil flowing through the pipeline responsive to: the determined fluid pressure at the first location, the determined fluid pressure at the second location, and the vertical elevation between the first location and the second location.

12. A method as defined in claim 11, further comprising the steps of:
determining fluid temperature at the first location along the vertically oriented extent of the bypass line; and
determining fluid temperature at the second location along the vertically oriented extent of the bypass line; and
wherein the step of estimating API gravity comprises the steps of:
estimating density of the crude oil flowing through the pipeline responsive to: the determined fluid pressure at the first location, the determined fluid pressure at the second location, and the vertical elevation between the first location and the second location,
estimating specific gravity of the crude oil sample at standard condition responsive to: the estimated density, determined fluid temperature at the first location, and the determined fluid temperature at the second location to thereby estimate the specific gravity of the crude oil flowing through the pipeline, and
estimating API gravity of the crude oil flowing through the pipeline at standard condition responsive to the estimated specific gravity of the crude oil sample extracted into the bypass line.

13. A method as defined in claim 12, wherein the estimated API gravity is determined according to the following calculations:

$$\rho_c = \frac{P_2 - P_1}{h};$$

$$\gamma = \frac{\rho_c}{\rho_w};$$

$$\gamma_{STD} = \gamma[1 - \beta(T_2 - T_1)];$$

$$\text{Crude } API_{STD} = \left(\frac{141.5}{\gamma_{STD}} - 131.5\right); \text{ and}$$

wherein:
$\rho_c$ is the density of the crude oil,
$P_1$ is the determined fluid pressure at the first location,
$P_2$ is the determined fluid pressure at the second location,
h is the vertical elevation between the first and the second fluid pressure sensors,
$\gamma$ is the specific gravity of the crude oil at operating condition,
$\rho_w$ is the density of water,
$\gamma_{STD}$ is the specific gravity of the crude oil at standard condition,
$\beta$ is the coefficient of isobaric thermal expansion,
$T_1$ is the determined fluid temperature at the first location, and
$T_2$ is the determined fluid temperature at the second location.

14. A method as defined in claim 11,
wherein the pipeline is a primary crude oil delivery pipeline; and
wherein the bypass line is positioned adjacent a vertically oriented portion of the primary crude oil delivery pipeline having a downward flowing flowstream, the distal end portion of the bypass line is connected to a distal end portion of the vertically oriented extent of the pipeline at an angle of between approximately 15 degrees and 45 degrees, and the first and the second pressure sensors are positioned along the vertically oriented extent of the bypass line, to thereby negate a need for a fluid sampling pump.

15. A method as defined in claim 11, wherein the crude oil sample is a crude oil sample of dehydrated degassed crude oil, and wherein the bypass line is at least partially connected to a vertically oriented portion of the pipeline, the method further comprising the steps of:
opening a remotely operated valve to supply the crude oil sample to the bypass line, the crude oil sample flowing downward between the first location and the second location responsive to the step of opening the remotely operated valve and responsive to gravity; and
closing the remotely operated valve to substantially isolate the crude oil sample.

16. A method as defined in claim 15,
wherein the vertically oriented extent of the bypass line is vertically oriented at between approximately 40° to 90° to the horizon, the remotely operated valve is positioned downstream of the proximal end portion connection of the bypass line to the crude oil pipeline and upstream of the first location along the vertically oriented extent of the bypass line, the bypass line is interfaced with a pair of vertically spaced apart pipeline fluid taps, and the first and the second pressure sensors are positioned along the vertically oriented extent of the bypass line, to thereby negate a need for a fluid sampling pump;
wherein the proximal end portion of the bypass line is connected to the first pipeline tap;

wherein the distal end portion of the bypass line is connected to the second pipeline tap, the second pipeline tap positioned vertically below and spaced apart from the first pipeline tap; and wherein the second pipeline tap is maintained open when determining fluid pressures of crude oil at the first and the second locations to apply fluid pressure to the crude oil sample associated with fluid pressure of the fluid stream flowing through the pipeline adjacent the distal end portion of the bypass line.

17. A method as defined in claim 11, wherein the crude oil flowing through the pipeline comprises a mixture of a plurality of specific crude oil grades defining a complex crude oil blend received from a processing facility and provided to the processing facility by a plurality of oil wells each producing one of the plurality of crude oil grades, the method further comprising the steps of:

comparing the estimated API gravity of the crude oil flowing through the vertically oriented extent of the pipeline to at least one threshold value to determine if the API gravity has failed to meet the at least one threshold value; and adjusting the API gravity by adjusting a flow rate of one or more of the plurality of wells responsive to determining that the API gravity fails to meet or exceeds the at Least one threshold value to thereby maintain the API gravity above a preselected desired minimum value or within a preselected desired range limit.

18. A method as defined in claim 11, further comprising the steps of:

retrofitting the pipeline with a first aperture defining a first pipeline tap extending through an outer wall surface of the pipeline adjacent a vertically oriented extent of the pipeline;

retrofitting the pipeline with a second aperture defining a second pipeline tap extending through an outer wall surface of a vertically oriented extent of the pipeline, the second pipeline tap positioned vertically below the first pipeline tap;

connecting the proximal end portion of the bypass line to the first pipeline tap; and connecting the distal end portion of the bypass line to the second pipeline tap.

19. A system to estimate and manage flowing fluid characteristics of a fluid stream flowing through a pipeline in a processing facility in real-time, the system comprising:

at least a portion of a pipeline for transporting dehydrated degassed crude oil including a horizontally oriented extent at least partially horizontally oriented and a vertically oriented extent substantially vertically oriented so that the crude oil flowing through the vertically oriented extent flows downward through the vertically oriented extent of the pipeline;

a bypass line having a proximal end portion connected to the horizontally oriented extent of the pipeline to receive a portion of the fluid stream flowing through the pipeline defining the crude oil sample and having a distal end portion connected to the vertically oriented extent of the pipeline to reintroduce the crude oil sample back into the fluid stream of the pipeline;

at least one first sensor connected to a first portion of the bypass line at a first location along an extent of the bypass line to provide at least one signal indicative of pressure and temperature of the crude oil at the first location;

at least one second sensor connected to a second portion of the bypass line at a second location along the extent of the bypass line to provide at least one signal indicative of pressure and temperature of the crude oil at the second location, the second location substantially vertically spaced apart from and vertically below the first location, the at least one first and the at least one second sensors having a preselected vertical elevation therebetween;

a remotely operated valve interfaced with the bypass line and positioned downstream of the proximal end portion connection of the bypass line to the pipeline and upstream of the first location along the extent of the bypass line; and a controller to estimate and manage flowing fluid characteristics of the crude oil including a processor and memory coupled to the processor, the controller in communication with the at least one first sensor and the at least one second sensor.

20. A system as defined in claim 19, further comprising:

crude oil analysis and management program product stored in the memory of the controller, the crude oil analysis and management program product including instructions that when executed by the processor of the controller, cause the controller to perform the operations of:

determining fluid pressure and temperature of the crude oil at the first location responsive to the at least one signal provided by the at least one first sensor, determining fluid pressure and temperature of the crude oil at the second location responsive to the at least one signal provided by the at least one second sensor, estimating density of the crude oil flowing through the at least a portion of the pipeline responsible to: the determined fluid pressure at the first location, the determined fluid pressure at the second location, and the vertical elevation between a pressure sensor portion of the at least one first sensor and a pressure sensing portion of the at least one second sensor, estimating specific gravity of the crude oil flowing through the at least a portion of the pipeline at standard condition responsive to the estimated density of the crude oil, determined fluid temperature at the first location, and the determined fluid temperature at the second location, and estimating API gravity of the crude oil flowing through the at least a portion of the pipeline at standard condition responsive to the estimated specific gravity of the crude oil flowing through the pipeline.

21. A system as defined in claim 20, wherein the system further comprises a plurality of flow control valves each in communication with the controller and each separately positioned to control a flow rate of crude oil entering the at least a portion of the pipeline received from a processing facility and provided to the processing facility by a plurality of oil wells;

wherein the crude oil comprises a complex crude blend including a plurality of crude grades provided by the plurality of oil wells; and wherein the operations further include:

comparing the estimated API gravity of the crude oil flowing through the vertically oriented extent of the at least a portion of the pipeline to at least one threshold value to determine if the API gravity has failed to meet the at least one threshold value to thereby maintain the API gravity above a preselected desired minimum value or within a preselected desired range limit, and adjusting the API gravity by adjusting the flow rate of one or more of the plurality of wells responsive to determining that the API gravity fails to meet or substantially exceeds the at least one threshold value.

22. A system as defined in claim 19,
wherein the pipeline is a primary crude oil delivery pipeline; and
wherein the bypass line is positioned adjacent the vertically oriented extent of the pipeline, and the first and the second pressure sensors are positioned along the vertically oriented extent of the bypass line, to thereby negate a need for a fluid sampling pump.

23. A system as defined in claim 22,
wherein the proximal end portion of the bypass line interfaces with a fluid collection extension extending into the fluid stream of the at least partially horizontally oriented extent, the fluid collection extension including a conical flange having an inlet oriented substantially parallel with the fluid stream; and
wherein the distal end portion of the bypass line is connected to a distal end portion of the vertically oriented extent of the pipeline at an angle of between approximately 15 degrees and 45 degrees.

24. A system as defined in claim 19,
wherein the at least one first sensor is a combined first pressure and temperature transducer; and
wherein the at least one second sensor is a combined second pressure and temperature transducer.

25. Crude oil analysis and management program product stored in a tangible computer readable medium to estimate and manage flowing fluid characteristics of a fluid stream flowing through a pipeline in real-time, the program product including instructions that when executed by a computer, cause the computer to perform the operations of:
determining fluid pressure of crude oil at a first location along a vertically oriented extent of a bypass line carrying a sample of crude oil extracted from a fluid stream flowing through a pipeline responsive to at least one signal provided by at least one first sensor associated with the first location, the bypass line positioned adjacent a vertically oriented extent of the pipeline, the bypass line having a proximal end portion connected to the pipeline to receive a portion of the fluid stream flowing through the pipeline defining the crude oil sample and having a distal end portion positioned to reintroduce the crude oil sample back into the fluid stream of the pipeline;
determining fluid pressure of the crude oil at a second location responsive to at least one signal provided by at least one second sensor associated with the second location, the second location substantially vertically separated from the first location, the at least one second sensor substantially vertically separated from the at least one first sensor by a vertical elevation; and
estimating API gravity of the crude oil flowing through the vertically oriented extent of the pipeline responsive to: the determined fluid pressure at the first location, the determined fluid pressure at the second location, and the vertical elevation between the at least one first sensor and the at least one second sensor.

26. Program product as defined in claim 25, wherein the operations further comprise:
determining fluid temperature of the crude oil at the first location along the vertically oriented extent of the bypass line responsive to the at least one signal provided by the at least one first sensor;
determining fluid temperature of the crude oil at the second location along the vertically oriented extent of the bypass line responsive to the at least one signal provided by the at least one second sensor; and
wherein the step of estimating API gravity comprises the steps of:
estimating density of the crude oil flowing through the vertically oriented extent of the pipeline,
estimating specific gravity of the crude oil flowing through the vertically oriented extent of the pipeline at standard condition responsive to: the estimated density of the crude oil, determined fluid temperature at the first location, and the determined fluid temperature at the second location, and
estimating the API gravity of the crude oil is at standard condition responsive to the estimated specific gravity of the crude oil sample extracted into the bypass line.

27. Program product as defined in claim 25,
wherein the crude oil comprises a complex crude blend including a plurality of crude grades received from a processing facility and provided to the processing facility by a plurality of wells; and
wherein the operations further comprise:
comparing the estimated API gravity of the crude oil flowing through the vertically oriented extent of the pipeline to at least one threshold value to determine if the API gravity has failed to meet the at least one threshold value to thereby maintain the API gravity above a preselected desired minimum value or within a preselected desired range limit, and
providing an adjustment signal to adjust a flow rate of one or more of the plurality of wells each having at least one flow control valve each separately positioned to control a flow rate of crude oil entering the pipeline received from a corresponding separate one of the plurality of wells.

28. Program product as defined in claim 25,
wherein the crude oil comprises a complex crude blend including a plurality of crude grades received from a processing facility and provided to the processing facility by a plurality of wells; and
wherein the operations further comprise:
comparing the estimated API gravity of the crude oil flowing through the vertically oriented extent of the pipeline to at least one threshold value to determine if the API gravity has exceeded the at least one threshold value to thereby maintain the API gravity within a preselected desired range limit, and
providing an adjustment signal to adjust a flow rate of one or more of the plurality of wells responsive to determining that the API gravity exceeds the at least one threshold value.

29. Program product as defined in claim 25, wherein the estimated API gravity is determined according to the following calculations:

$$\rho_c = \frac{P_2 - P_1}{h};$$

$$\gamma = \frac{\rho_c}{\rho_w};$$

$$\gamma_{STD} = \gamma[1 - \beta(T_2 - T_1)];$$

$$\text{Crude } API_{STD} = \left(\frac{141.5}{\gamma_{STD}} - 131.5\right); \text{ and}$$

wherein:
$\rho_c$ is the density of the crude oil,
$P_1$ is the determined fluid pressure at the first location, $P_2$ is the determined fluid pressure at the second location, h is the vertical elevation between the at least one first pressure sensor and the at least one second pressure sensor, γ is the specific gravity of the crude oil at operating condition, $\rho_w$ is the density of water, $\gamma_{STD}$ is the specific gravity of the crude oil at standard condition, β is the coefficient of isobaric thermal expansion, $T_1$ is the determined fluid temperature at the first location, and $T_2$ is the determined fluid temperature at the second location.

30. Program product as defined in claim 25, wherein the operations further comprise gathering the crude oil sample when a remotely operated valve is opened using a fluid collection extension extending into the fluid stream flowing in the preselected section of the existing pipeline;

wherein the fluid collection extension includes a conical flange having an inlet oriented substantially parallel with the fluid stream; and wherein the distal end portion of the bypass line is connected to the distal end portion of the vertically oriented extent of the pipeline at an angle of between approximately 15 degrees and 45 degrees.

* * * * *